(12) United States Patent
De Lange et al.

(10) Patent No.: US 8,987,478 B2
(45) Date of Patent: Mar. 24, 2015

(54) PROCESS FOR THE PREPARATION OF A STATIN PRECURSOR

(71) Applicant: DSM Sinochem Pharmaceuticals Netherlands B.V., Delft (NL)

(72) Inventors: Ben De Lange, Echt (NL); Dennis Heemskerk, Echt (NL); Karin Henderika Maria Bessembinder, Echt (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

(21) Appl. No.: 14/363,980

(22) PCT Filed: Dec. 6, 2012

(86) PCT No.: PCT/EP2012/074688
§ 371 (c)(1),
(2) Date: Jun. 9, 2014

(87) PCT Pub. No.: WO2013/083718
PCT Pub. Date: Jun. 13, 2013

(65) Prior Publication Data
US 2014/0357864 A1   Dec. 4, 2014

(30) Foreign Application Priority Data
Dec. 9, 2011  (EP) ..................................... 11192748

(51) Int. Cl.
C07D 319/06 (2006.01)
C07D 417/12 (2006.01)
C07D 233/96 (2006.01)
C07D 405/12 (2006.01)

(52) U.S. Cl.
CPC ............ *C07D 417/12* (2013.01); *C07D 233/96* (2013.01); *C07D 405/12* (2013.01); *C07D 319/06* (2013.01)
USPC ........................................................ 549/375

(58) Field of Classification Search
USPC .......................................... 544/297; 549/375
See application file for complete search history.

(56) References Cited

FOREIGN PATENT DOCUMENTS

WO    WO 02/06266      1/2002
WO    WO 02/098854    12/2002

OTHER PUBLICATIONS

International Search Report for PCT/EP2012/074688 mailed Jan. 22, 2013.

*Primary Examiner* — Kristin Vajda
(74) *Attorney, Agent, or Firm* — Nixon & Vanderhye P.C.

(57) ABSTRACT

The present invention relates to a process for the preparation of a precursor for the synthesis of hexanoic acid derived statins and to the use of said precursor in the manufacture of a medicament.

4 Claims, No Drawings

PROCESS FOR THE PREPARATION OF A STATIN PRECURSOR

This application is the U.S. national phase of International Application No. PCT/EP2012/074688, filed 6 Dec. 2012, which designated the U.S. and claims priority to EP Application No. 11192748.9, filed 9 Dec. 2011, the entire contents of each of which are hereby incorporated by reference.

FIELD OF THE INVENTION

The present invention relates to a process for the preparation of a precursor for the synthesis of hexanoic acid derived statins and to the use of said precursor in the manufacture of a medicament.

BACKGROUND OF THE INVENTION

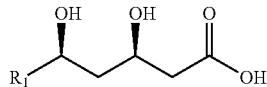

(1)

Hexanoic acid derived statins of general formula (1) or salts thereof inhibit the enzyme 3-hydroxy-3-methylglutaryl-coenzyme A reductase (HMG-CoA reductase) and are thus useful as a hypolipidemic and hypocholesterolemic agents.

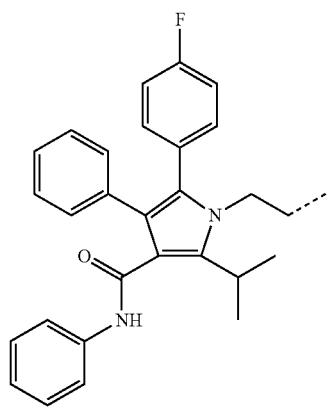

(A)

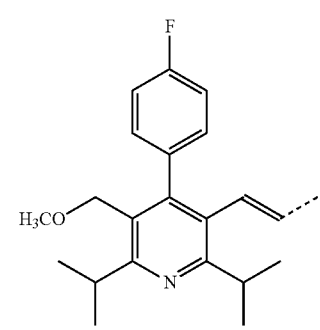

(C)

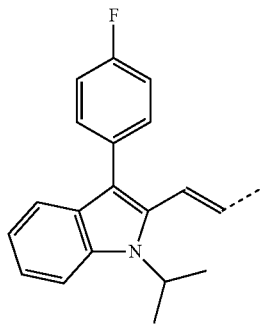

(F)

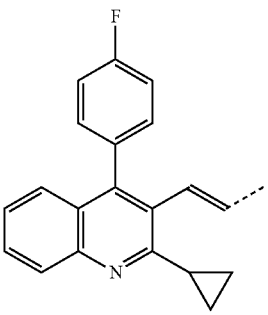

(P)

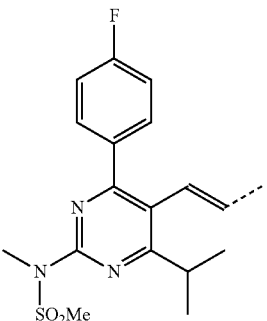

(R)

Examples of these statins are atorvastatin wherein $R_1$ is a radical of formula (A), cerivastatin wherein $R_1$ is a radical of formula (C), fluvastatin wherein $R_1$ is a radical of formula (F), pitavastatin wherein $R_1$ is a radical of formula (P) and rosuvastatin wherein $R_1$ is a radical of formula (R).

For the introduction of the chiral part of the abovementioned molecules, intermediates of general formula (2) play a pivotal role.

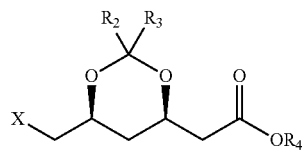

(2)

In the compounds of general formula (2) X stands for halogen and $R_2$ and $R_3$ each independently stand for an alkyl with for instance 1 to 12 carbon atoms and $R_2$ and $R_3$ may form a ring together with the carbon atom to which they are bound. The group $R_4$ is a carboxylic acid protecting group. For preparative purposes, $R_4$ must be a group that can be easily removed after formation of the statin structure. Suitable groups in this respect have proven to be sec-butyl, tert-butyl, iso-propyl and the like. In WO 02/06266 a procedure is disclosed for the preparation of compounds of formula (2) wherein $R_4$ is a methyl group, starting from a compound of general formula (3), with X is defined as above, by reaction with commercially available dimethoxypropane.

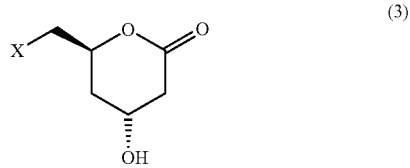
(3)

Unfortunately methyl protection is less suitable in the subsequent chemistry towards statins. To this end also the preparation of alternate esters that are preferred in view of ease of removal of impurities, reduction of side-reactions and/or stability is disclosed in WO 02/06266. However, this approach requires three additional reaction steps, namely hydrolysis of the methyl ester, activation of the resulting acid and conversion to the ester. Hence, there is a need for an improved approach for the synthesis of compounds of general formula (2) wherein $R_4$ is not methyl.

DETAILED DESCRIPTION OF THE INVENTION

In a first aspect of the invention, there is provided a method for the preparation of a compound of general formula (2)

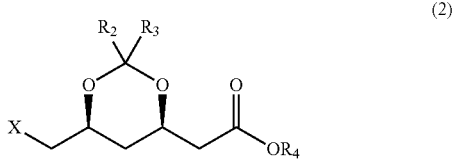
(2)

comprising contacting a compound of general formula (3)

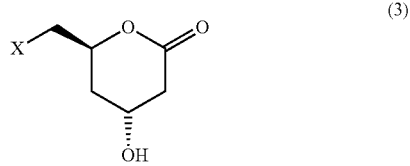
(3)

with an alcohol of general formula $R_4$—OH and an acetalization agent.

In the context of the present invention X refers to a halogen atom such as bromine, chlorine, fluorine or iodine, preferably bromine or chlorine. $R_2$ and $R_3$ each independently stand for an alkyl with for instance 1 to 12 carbon atoms, preferably 1 to 6 carbon atoms, an alkenyl with for instance 1 to 12 carbon atoms, preferably 1 to 6 carbon atoms, a cycloalkyl with for instance 3 to 7 carbon atoms, a cycloalkenyl with for instance 3 to 7 carbon atoms, an aryl with for instance 6 to 10 carbon atoms or an aralkyl with for instance 7 to 12 carbon atoms, each of $R_2$ and $R_3$ may be substituted and wherein $R_2$ and $R_3$ may form a ring together with the carbon atom to which they are bound. The groups $R_2$ and $R_3$ are for example halogens or hydrocarbon groups with for instance 1 to 10 carbon atoms, optionally containing one or more heteroatoms, for instance Si, N, P, O, S, F, Cl, Br or I. In practice, $R_2$=$R_3$ is methyl is most preferred. In the compound of general formula (2) $R_4$ is an alkyl or alkenyl group with 2 to 6 carbon atoms. Such relatively small substituents are favorable since they have a high so-called 'carbon economy', i.e. the use of organic material is lower than is the case with more complex protecting groups. Suitable examples are allyl, iso-butenyl, n-butyl, sec-butyl, tert-butyl, ethyl, 2-methyl-3-pentyl, 4-methyl-1-pentyl, 4-methyl-2-pentyl, n-propyl, iso-propyl or vinyl. The alcohol $R_4$—OH may be added in stoichiometric amounts but also larger amounts and the alcohol $R_4$—OH may even be present as solvent.

In one embodiment the method is carried out in the presence of an acid such as an inorganic or organic acid. Suitable acids are acetic acid, formic acid, hydrobromic acid, hydrochloric acid, methanesulphonic acid, sulfuric acid, p-toluenesulphonic acid and the like.

In another embodiment said acetalization agent is an acetal, an alkoxy-alkene or a ketone. Suitable examples of acetalization agents are acetone, cyclohexanone, cyclopentanone, dimethoxypropane, 2-ethoxypropene, 2-methoxypropene and 3-pentanone.

The method of the first aspect of the invention may be carried out at temperatures ranging from −20° C. to 150° C., preferably ranging from 0° C. to 100° C., more preferably ranging from 10° C. to 70° C. Suitable reaction times are from 10 min to 48 h, preferably from 30 min to 24 h, more preferably from 1 h to 18 h.

In still another embodiment, the compound of general formula (2) is isolated. This may be achieved by addition of water or an aqueous solution and optional neutralization by means of addition of a base such as carbonates, hydrogen carbonates, hydroxides and the like. The organic phase of the mixture thus obtained may be separated from the aqueous phase and optionally further purified by washing with water or an aqueous solution. Final isolation of the compound of general formula (2) from the organic phase is achieved by crystallization, precipitation, evaporation of the organic phase or combinations thereof. The resulting compound of general formula (2) may optionally be re-crystallized or purified by distillation.

The starting material of general formula (3) may be prepared according to procedures known to the skilled person, such as for instance described in EP 1404844. The method of the first aspect of the invention has the advantage that a variety of groups $R_4$ can be introduced in a single step without the need to perform multiple steps such as first preparing the methyl ester, hydrolyzing said methyl ester and introducing an alternate ester group. Such additional steps have the disadvantage of reducing overall yield, introducing unwanted impurities and/or reducing optical purity through racemization. Consequently the products of general formula (2) obtained by the method of the present invention are isolated in unprecedented high yields and are of high purity. For example, as a result of the method of the present invention, methanol, a contaminant known for its detrimental effect in pharmaceutical preparations, is not or hardly found in the final product. Thus, typical amounts of methanol in preparations according to the method of the present invention of the product of general formula (2) or the statins such as atorvastatin, cerivastatin, fluvastatin, pitavastatin or rosuvastatin derived from (2) are from 10 ppm to 500 ppm, preferably from 5 ppm to 200 ppm, more preferably from 1 ppm to 50 ppm and most preferably from 10 ppb to 500 ppb.

In a second aspect of the invention there is disclosed the use of a compound of general formula (2) obtained according to the first aspect of the invention in the manufacture of an antilipemic medicament. Suitably, the compound of general formula (2) is converted into a statin of formula (1) with $R_1$ is a radical of formula (A), (C), (F), (P) or (R) as defined above.

In a first embodiment of the second aspect, the compound of general formula (2) is reacted with a thiol compound of general formula $R_5$—S—Y to give a compound of general formula (2) with X is —$SR_5$ and $R_2$, $R_3$ and $R_4$ as defined above. In the compound of general formula $R_5$—S—Y, Y represents hydrogen (a proton) or another cation like, for example, an alkali metal ion, like sodium or potassium or lithium cation, or an ammonium ion, like tetraalkylammonium, or a phosphonium ion, like tetraalkylphosphonium. $R_5$ is an aryl group that for instance is suitable for a one-pot or modified Julia-Kocienski olefination. Suitable aryl groups are e.g. described in P. R. Blakemore, J. Chem. Soc., Perkin Trans. 1, 2002, 2563. Preferred aryl groups include tetrazole, substituted phenyl and benzimidazole type compounds. Specific examples of preferred aryl groups include, pyridine-2-yl, pyrimidin-2-yl, benzothiazol-2-yl, 1-methyl-1H-tetrazol-5-yl, 1-phenyl-1H-tetrazol-5-yl, 1-tert-butyl-1-H-tetrazol-5-yl, 3,5-bis(trifluoromethyl)phenyl-1-yl, 1-methylimidazol-2-yl, benzimidazol-2-yl, 4-methyl-1,2,4-triazol-3-yl and iso-quinolin-1-yl. Most preferred aryl groups are 1-methyl-1H-tetrazol-5-yl, 1-phenyl-1H-tetrazol-5-yl, 1-tert-butyl-1H-tetrazol-5-yl, benzothiazol-2-yl, and 3,5-bis(trifluoromethyl) phenyl-1-yl. The reaction to obtain the compound of general formula (2) with X is —$SR_5$ can be performed in a solvent or without the presence of a solvent. Suitable solvents are dimethylsulfoxide (DMSO), N-methyl pyrrolidone (NMP), dimethylformamide (DMF), sulfolane, acetonitrile, glymes (alkyl-capped or uncapped mono-, oligo-, or poly-ethylene glycol ethers of varying chain length) or other polar non-protic solvents or alcohols like methanol, ethanol, 2-propanol, or halogenated hydrocarbons like dichloromethane, chloroform, 1,2-dichloroethane, optionally in combination with non-polar solvents like toluene or methyl tert-butyl ether (MTBE). It is also possible to use biphasic solvent systems consisting of an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). The amounts of reagents can be chosen from a wide range. It is preferred to use a rate-enhancing excess of thiol compound, as the excess thiol that remains after reaction with the halomethyl derivative can be easily removed by washing with water at high pH. The molar amount of thiol to halogen compound generally is about 0.5 to 1 or higher, preferably 1 to 1 or higher, more preferably 1.1 to 1 or higher. Generally, the amount of thiol to halogen compound will be 3 to 1 or lower, preferably 2 to 1 or lower, most preferably 1.5 to 1 or lower. Preferably excess thiol is recovered for re-use which is easily achieved with the thiols of the present invention. It was unexpected, that the thio-ether compound of general formula (2) with X is —$SR_5$ could be prepared in this way, because a nucleophilic attack on a halomethyl group (in particular a chloromethyl group) in the presence of an alkoxy substituent in beta-position to the halogen is known to be extremely difficult [cf. a) Methoden der Organischen Chemie (Houben-Weyl), vol. V/4, 1960, p. 700; b) M. E. Jung et al, J. Org. Chem. 1998, 63, 347-355 and ref. 17 cited therein; c) D. G. Bourke et al., Aust. J. Chem. 1996, 49, 425-434]. This holds especially in cases where said alkoxy substituent is part of a cyclic ether moiety like the 1,3-dioxane moiety as exemplified in the compound of formula (2).

In a second embodiment, the thio-ether compound of general formula (2) with X is —$SR_5$ obtained in the first embodiment is oxidized in manners known in the art, for example by oxidation with hydrogen peroxide or other oxidants like peracids (e.g. 3-chloroperoxybenzoic acid, peroxyacetic acid, monoperoxyphthalic acid), bleach, tert-BuOCl, perborates, N-oxides, permanganate, chromate, chlorate, bromate, perchlorate, periodate, tert-butyl hydroperoxide, oxone, peroxodisulfates and air/oxygen. If necessary, the oxidation can be carried out in the presence of an appropriate catalyst, such as salts or oxides of the metals V, Ce, Mn, Ni, Fe, Cu, Os, Mo, W, Re, or Ru or organic catalysts like iso-butyraldehyde in the case of air/oxygen or tetramethylpiperidine N-oxide (TEMPO) in the case of bleach. The resulting sulfones are of general formula (2) with X is —$S(O)_2R_5$ respectively, with $R_2$, $R_3$, $R_4$, and $R_5$ as defined above. The oxidation generally is performed in a solvent, such as dichloromethane, chloroform, 1,2-dichloroethane, methanol, ethanol, 2-propanol, acetonitrile, acetic acid, toluene, water, NMP, DMSO, DMF, tetrahydrofuran (THF), or MTBE. It is also possible to use biphasic solvent systems consisting of an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). Another class of suitable solvents comprises ionic liquids like, for example, 1,3-dialkyl imidazolium salts or N-alkyl pyridinium salts of acids like hexafluorophosphoric acid or tetrafluoroboric acid or trifluoromethane sulfonic acid, or with $(CF_3SO_2)_2N^-$ as anionic counterpart. Generally, a reaction temperature of about −20° C. or higher is effective. Preferably, a temperature of about 0° C. or higher is applied, more preferably a temperature close to ambient temperature (18-25° C. i.e. around 20° C.). A temperature of about 150° C. or lower generally is effective to bring about the oxidation. Generally, the reaction temperature will be about 100° C. or lower, more preferably about 60° C. or lower, most preferably about 40° C. or lower. The molar amount of oxidant to thio-ether generally is about 1 to 1 or higher, preferably about 2 to 1 or higher, more preferably about 3 to 1 or higher. Generally, the amount of terminal oxidant to thio-ether will be about 20 to 1 or lower, preferably about 10 to 1 or lower, most preferably about 5 to 1 or lower. The sulfone of general formula (2) with X is —$S(O)_2R_5$ can be isolated by aqueous extraction of excess oxidant/catalyst and subsequent removal of the solvent by evaporation. If water-miscible solvents like alcohols or aprotic polar solvents are applied as reaction medium, the reaction mixture can be partitioned between an aqueous and an organic phase prior to this operation, in order to extract the solvent to the aqueous phase. If ionic liquids are applied as reaction medium, the sulfone can be isolated by extraction with an organic solvent immiscible with the ionic liquid, followed by evaporation of the solvent. Alternatively, the sulfone can be isolated from the reaction mixture by precipitation or crystallization, e.g. by addition of (or solvent switch to) an anti-solvent like hexane, heptane, iso-octane, or water. If desired, further purification can be performed by chromatography or re-crystallization.

In a third embodiment, the sulfone of general formula (2) with X is —$S(O)_2R_5$ is treated with an aldehyde $R_6$—CH=O, in which $R_6$ is chosen so as to obtain suitable precursors to useful statin-type compounds including pitavastatin, rosuvastatin, fluvastatin, and cerivastatin, or in which $R_6$ is a suitable precursor to these moieties (cf. WO 2002/098854 and WO 2001/096311). Preferred examples of aldehyde $R_6$—CH=O are 4-(4-fluorophenyl)-2,6-diisopropyl-5-(methoxymethyl)nicotinaldehyde, 3-(4-fluorophenyl)-1-isopropyl-1H-indole-2-carbaldehyde, 2-cyclopropyl-4-(4-fluorophenyl)-quinoline-3-carbaldehyde and N-(4-(4- fluorophenyl)-5-formyl-6-isopropylpyrimidin-2-yl)-N-methylmethanesulfonamide as these aldehydes are the precursors for cerivastatin, fluvastatin, pitavastatin and rosuvastatin, respectively. This reaction preferably is carried out in the presence of a base, preferred examples of which are lithium hydride, potassium hydride, sodium hydride, lithium hexamethyldisilazane, sodium hexamethyldisilazane, potassium hexamethyldisilazane, solid potassium hydroxide, solid sodium hydroxide, metal alkoxides, such as sodium methoxide, lithium methoxide and potassium methoxide, lithium tert-butoxide, potassium tert-butoxide, sodium tert-butoxide, lithium bis-trimethylsilylamide, sodium bis-trimethylsilylamide, potassium bis-trimethylsilylamide, sodium amide, P4-tBu and 1,8-diazabicyclo[5.4.0]undec-7-ene and the like.

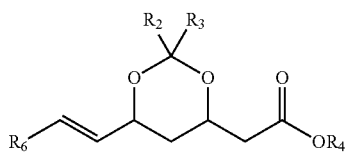

(4)

Following the Julia-Kocienski olefination, the resulting product (4) may be isolated and purified after which it is de-protected to give hexanoic acid derived statins of general formula (1) wherein $R_1$ is a radical of formula (C), (F), (P) or (R) or salts thereof. Alternatively, deprotection may be carried out without isolation and/or purification of intermediate product (4). Deprotection is carried out according to procedures known to the skilled person, for instance by using acid such as hydrochloric acid as described in U.S. Pat. No. 6,844,437 or WO 2007/000121.

EXAMPLES

Example 1

4R,6S)-6-(Chloromethyl)-2,2-dimethyl-1,3-dioxan-4-yl)acetic acid sec-butyl ester (2; X=Cl, $R_2$=$R_3$=—$CH_3$, $R_4$=—$CH(CH_3)CH_2CH_3$ (4R,6S)-6-(Chloromethyl)-4-hydroxytetrahydropyran-2-one (EP 1404844, 200 g, 1.22 mol) was dissolved in sec-butanol (1.9 L). To the mixture was added acetic acid (5.6 mL). The reaction mixture was stirred at 60° C. for 24 h and cooled to 20-25° C. Next, 240 mL of dimethoxypropane (1.6 equiv., 1.96 mol) was added in 0.5 h. After stirring for 3.5 h, 500 mL of 10 m/m % aqueous $NaHCO_3$ (pH≈8 after addition), 800 mL of water and 800 mL of ethyl acetate were added. The mixture was stirred for 15 minutes and the phases were separated. The organic phase was washed again with 500 mL of water. The organic phase was evaporated, re-dissolved in 500 mL of ethyl acetate and washed with 500 mL of water. The organic phase was separated and dried with $Na_2SO_4$. After evaporation, 297.5 g of the title product was obtained as a brown liquid (87% yield based on (4R,6S)-6-(chloromethyl)-4-hydroxytetrahydropyran-2-one). $^1$H NMR (300 MHz, $CDCl_3$) δ 4.88 (d, 1H), 4.40-4.25 (m, 1H), 4.16-3.99 (m, 1H), 3.46 (ddd, 2H), 2.55-2.30 (m, 2H), 1.78 (dt, 1H), 1.67-1.50 (m, 2H), 1.47 (s, 3H), 1.39 (s, 3H), 1.34-1.16 (m, 4H), 0.90 (t, 3H).

Example 2

(4R,6S)-6-(Chloromethyl)-2,2-dimethyl-1,3-dioxan-4-yl)acetic acid 1,3-dimethylbutyl ester 2; X=Cl, $R_2$=$R_3$=—$CH_3$, $R_4$=—$CH(CH_3)CH_2CH(CH_3)_2$ Methanesulphonic acid (4.8 g) was added to 500 mL of 4-methyl-2-pentanol. Then (4R,6S)-6-(chloromethyl)-4-hydroxytetrahydropyran-2-one (EP 1404844, 164.7 g, 1.22 mol) was added in portions at 20-25° C. in about 1 h during which the starting material dissolved. The reaction mixture was stirred at 20-25° C. for 18 h, followed by addition of 2,2-dimethoxypropane (156.2 g, 1.5 mol) in 0.5 h. The reaction mixture was stirred for 0.5 h. Next 250 mL of saturated aqueous $NaHCO_3$ was added and the phases were separated. The organic phase was washed with 250 mL of saturated aqueous $NaHCO_3$. The organic phase was evaporated to give 307.0 g of the title compound as a brownish oil (≈100% yield, uncorrected for assay based on (4R,6S)-6-(chloromethyl)-4-hydroxytetrahydropyran-2-one. This oil was used in the follow up reaction without further purification. $^1$H NMR (300 MHz, $CDCl_3$) δ 5.10-4.90 (m, 1H), 4.40-4.28 (m, 1H), 4.16-3.99 (m, 1H), 3.52 (dd, 1H), 2.41-2.51 (m, 2H), 1.78 (dt, 1H), 1.62-1.57 (m, 2H), 1.47 (s, 3H), 1.41 (s, 3H), 1.34-1.16 (m, 6H), 0.85-1.00 (m, 6H).

Example 3

2-(4R,6S)-6-((Benzo[d]thiazole-2-ylthio)methyl)-2,2-dimethyl-1,3-dioxan-4-yl)acetic acid sec-butyl ester A reactor was charged with (4R,6S)-6-(chloromethyl)-2,2-dimethyl-1,3-dioxan-4-yl)acetic acid sec-butyl ester (2; X=Cl, $R_2$=$R_3$=—$CH_3$, $R_4$=—$CH(CH_3)CH_2CH_3$; 297.5 g; 1.07 mol) and N-methylpyrrolidone (1160 mL). To this solution was added 2-mercapto-1H-benzothiazole (214 g; 1.2 equiv. 1.28 mol), $NaHCO_3$ (117 g; 1.3 equiv., 1.39 mol) and tetra-n-butyl ammonium bromide (0.69 g). The reaction mixture was stirred for 23 h at 90° C. Then the reaction mixture was cooled to room temperature, diluted with 1.5 L of methyl-tert-butyl ether and washed with 1 L of saturated aqueous $NaHCO_3$. The organic phase was washed again with 2×700 mL of saturated aqueous $NaHCO_3$ and 2×700 mL of water. The resulting brown organic layer was treated with 20 g active carbon. After removal of the carbon by filtration, the organic phase was concentrated to give the title product as a yellow oil. Yield 301.8 g (69%). $^1$H NMR (300 MHz, $CDCl_3$) δ 7.91 (d, 1H), 7.76 (d, 1H), 7.49-7.39 (m, 1H), 7.36-7.28 (m, 1H), 4.96-4.77 (m, 1H), 4.40-4.21 (m, 2H), 3.53 (add, 2H), 2.46 (ddd, 2H), 1.84 (dt, 1H), 1.65-1.49 (m, 2H), 1.46 (s, 3H), 1.39 (s, 3H), 1.36-1.22 (m, 1H), 1.20 (dd, 3H), 0.89 (m, 3H).

Example 4

2-(4R,6S)-6-((Benzo[d]thiazole-2-ylthio)methyl)-2,2-dimethyl-1,3-dioxan-4-yl)acetic acid 1,3-dimethylbutyl ester A reactor was charged with (4R,6S)-6-(chloromethyl)-2,2-dimethyl-1,3-dioxan-4-yl)acetic acid 1,3-dimethylbutyl ester (61.2 g; 0.20 mol) and 60 mL of N-methylpyrrolidone. To this solution was added 2-mercapto-1H-benzothiazole (36.7 g; 1.1 equiv.; 0.22 mol), NaHCO₃ (21.0 g; 1.25 equiv., 0.25 mol) and tetra-n-butyl ammonium bromide (0.2 g). The reaction mixture was stirred for 28 h at 110-115° C. The reaction mixture was cooled to 20-25° C. and 300 mL of methyl-tert-butyl ether was added. The precipitated salts were filtered and the salts were washed with 100 mL of methyl-tert-butyl ether. The combined filtrates were washed with 200 mL of saturated aqueous NaHCO₃. The resulting brown organic phase was treated with 2 g active carbon and dried over Na₂SO₄. After removal of the carbon and Na₂SO₄ by filtration, the organic phase was concentrated to give the title compound as a yellow oil. Yield 80.0 g (91%). ¹H NMR (300 MHz, CDCl₃) δ 7.85 (d, 1H), 7.60 (d, 1H), 7.50-7.38 (m, 1H), 7.33-7.25 (m, 1H), 5.09-4.95 (m, 1H), 4.40-4.20 (m, 2H), 3.51 (ddd, 2H), 2.46 (ddd, 2H), 1.84 (dt, 1H), 1.68-1.49 (m, 2H), 1.46 (s, 3H), 1.40 (s, 3H), 1.36-1.22 (m, 1H), 1.23-1.18 (m, 4H), 0.90-0.87 (m, 6H).

Example 5

2-((4R,6S)-6-((Benzo[d]thiazol-2-ylsulfonyl)methyl)-2,2-dimethyl-1,3-dioxan-4-yl)acetic acid sec-butyl ester A) Procedure Using m-CPBA
2-(4R,6S)-6-((Benzo[d]thiazole-2-ylthio)methyl)-2,2-dimethyl-1,3-dioxan-4-yl)acetic acid sec-butyl ester (2.48 g, 6.0 mmol) and 1.9 g NaHCO₃ (22.8 mmol; 3.8 equiv.) were added to 50 mL of dichloromethane at 0° C. Then 4.1 g m-CPBA (16.8 mmol; 2.8 equiv.) was added slowly keeping the temperature below 5° C. (slightly exothermic). When addition was completed, the temperature was allowed to rise to 20-25° C. and stirring was continued for 18 h. The mixture was diluted with 50 mL of dichloromethane and the precipitated salts were removed by filtration. The organic phases were washed with 2×100 mL of 10 w/w % aqueous NaHSO₃ and 4×100 mL of 5 w/w % aqueous Na₂CO₃ After drying on Na₂SO₄, the dichloromethane was evaporated. The resulting thick oil was stirred in isopropanol to give the title compound as a white solid (0.54 g, yield 20%). ¹H NMR (300 MHz, CDCl₃) δ 8.22 (d, 1H), 8.01 (d, 1H), 7.70-7.51 (m, 2H), 4.85 (m, 1H), 4.59 (ddt, 1H), 4.40-4.24 (m, 1H), 3.87 (dd, 1H), 3.42 (dd, 1H), 2.45-2.35 (m, 2H), 1.71 (d, 1H), 1.43 (d, 2H), 1.36-1.33 (m, 4H), 1.18 (dd, 3H), 0.87 (dt, 3H), 0.78 (s, 3H).
B) Procedure Using Na₂WO₄.2H₂O and 30% H₂O₂
2-(4R,6S)-6-((Benzo[d]thiazole-2-ylthio)methyl)-2,2-dimethyl-1,3-dioxan-4-yl)acetic acid sec-butyl ester (4 g, 9.8 mmol) was dissolved in 20 mL of methanol and Na₂WO₄.2H₂O (0.3 g, 10 mol %) was added. Next, 3 mL of a 30% H₂O₂ solution was added in 1 h keeping the temperature below 25° C. and the pH at about 8.5 using aqueous 4M NaOH. After the addition was completed, the mixture was stirred for 18 h. The precipitated solid was isolated by filtration. The solid was dissolved in ethyl acetate and washed 2 times with 10 w/w % aqueous Na₂SO₃. The organic phase was evaporated and the resulting solid was re-crystallized from isopropanol to give the title compound as a white solid (2.46 g, yield 57%). NMR identical as given under procedure A using m-CPBA.
C) Procedure Using Na₂WO₄.2H₂O and 30% H₂O₂ (270 g Scale)
A reactor was filled with 2-(4R,6S)-6-((benzo[d]thiazole-2-ylthio)methyl)-2,2-dimethyl-1,3-dioxan-4-yl)acetic acid sec-butyl ester (270 g, 0.66 mol), Na₂WO₄.2H₂O (21.7 g; 10 mol %) and methanol (1940 mL). To this mixture was added in 2 h, 222 mL of a 30% H₂O₂ solution (3.3 equiv.), keeping the temperature at 20° C. and the pH at 8 using aqueous 4M NaOH. When the addition was completed, the reaction mixture was stirred for 23 h. The precipitated product was filtered and washed with methanol (100 mL). To the filtrate was added water (500 mL) to precipitate more solid and the product was filtered. The combined solids were dried to give 164 g of crude product. The crude material was re-crystallized from isopropanol, to give 125 g of the title compound. The filtrate was concentrated to about 150 mL to give another 19 g of title compound. In total 144 g of title compound (yield=41%) was obtained.

Example 6

2-((4R,6S)-6-((Benzo[d]thiazol-2-ylsulfonyl)methyl)-2,2-dimethyl-1,3-dioxan-4-yl)acetic acid 1,3-dimethylbutyl ester 2-(4R,6S)-6-((Benzo[d]thiazole-2-ylthio)methyl)-2,2-dimethyl-1,3-dioxan-4-yl)acetic acid 1,3-dimethylbutyl ester (32.8 g, 75 mmol) and NaHCO₃ (23.9 g; 285 mmol, 3.8 equiv.) were added to 300 mL of dichloromethane at 0° C. Then m-CPBA (51.8 g; 210 mmol; 2.8 equiv) was added slowly keeping the temperature below 5° C. (slightly exothermic). When addition was completed, the temperature was allowed to rise to 20-25° C. and stirred was continued for 18 h. After 3 h, 100 mL of dichloromethane was added. After 18 h again 100 mL of dichloromethane was added and the precipitated salts were removed by filtration and washed with 100 mL of dichloromethane. The organic phases were washed with 2×250 mL of 10 w/w % aqueous NaHSO₃ and 4×250 mL of 5 w/w % aqueous Na₂CO₃ After drying on Na₂SO₄, the dichloromethane was evaporated to give the title compound as an oil which slowly solidified (35.1 g, yield 98%). ¹H NMR (300 MHz, CDCl₃) δ 8.15 (d, 1H), 7.95 (d, 1H), 7.58-7.40 (m, 2H), 5.07-4.98 (m, 1H), 4.60-4.42 (m, 1H), 4.30-4.18 (m, 1H), 3.90 (ddd, 1H), 3.50-3.40 (dt, 1h), 2.42 (ddd, 2H), 1.76 (dt, 1H), 1.68-1.54 (m, 2H), 1.37 (s, 3H), 1.27 (s, 3H), 1.30-1.21 (m, 1H), 1.19-1.15 (m, 4H), 0.89-0.86 (m, 6H).

Example 7

2-((4R,6S)-6-((E)-2-(4-(4-Fluorophenyl)-6-isopropyl-2-(N-methylmethylsulfonamido)pyrimidin-5-yl)vinyl)-2,2-dimethyl-1,3-dioxan-4-yl)acetate, sec-butyl ester N-(4-(4-fluorophenyl)-5-formyl-6-isopropylpyrimidin-2-yl)-N-methylmethanesulfonamide (5.7 g, 16.3 mmol) and 2-((4R,6S)-6-((benzo[d]thiazol-2-ylsulfonyl)methyl)-2,2-dimethyl-1,3-dioxan-4-yl)acetate sec-butyl ester (8.0 g, 18.1 mmol) were added to 104 mL of tetrahydrofuran. The reaction mixture was heated until all the reagents were dissolved and then cooled to −70° C. At this temperature 27.2 mL of a NaHMDS solution (20% in tetrahydrofuran, total 27.2 mmol, 1.5 equiv.) was added in 1 h at −70° C. When dosing was completed, the reaction mixture was stirred for 1 h at −70° C. HPLC analysis showed 68% of product formed. The reaction mixture was quenched with 100 mL of 10% aqueous NH₄Cl, the aqueous phase was separated and the organic phase was washed 2 times with 100 mL of 10% aqueous NH₄Cl. Next, the organic phase was washed 3 times with water at pH 12 (using 1M aqueous NaOH). The organic phase was evaporated and the residue was crystallized from isopropanol to give the title compound ester as a solid. ¹H NMR (300 MHz, CDCl₃) δ 7.58 (dd, 2H), 7.01 (t, 2H), 6.45 (dd, 1H), 5.40 (dd, 1H), 4.81 (m, 1H), 4.44-4.18 (m, 2H), 3.54-3.47 (m, 3H), 3.47-3.38 (m, 3H), 3.35-3.25 (m, 1H), 2.37 (ddd, 2H), 1.59-1.43 (m, 4H), 1.41 (s, 3H), 1.33 (s, 3H), 1.20, (dd, 6H), 1.14 (d, 3H), 0.83 (t, 3H).

Example 8

Rosuvastatin-Ca 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate, sec-butyl ester (2.0 g, 3.46 mmol) was added to 40 mL of methanol. The mixture was heated to 35° C. until complete dissolution was obtained. The solution was cooled to 20° C. and 9 mL of 0.2 N HCl was added over a period of 2 h. The mixture was stirred for 18 h, followed by addition of 1 N NaOH in 15 min until a pH of 12. After stirring for 1 h, 0.2 g of dicalite was added and the mixture was filtered. The solution was concentrated to about 15 g, 10 mL of water was added and the mixture was concentrated to 15 g. Then 10 mL of water was added. To the obtained clear solution was added in portions over a period of 1 h, 7 mL of a solution of 4.5 w/w % Ca(OAc)₂.H₂O (1.2 equiv.) in water. Upon addition white precipitate was formed. After 1 h the precipitate was filtered and dried to give 1.34 g (2.68 mmol) of the calcium salt of rosuvastatin as a slightly yellow solid (yield 77%). ¹H NMR (300 MHz, DMSO) δ 7.72 (dd, 2H), 7.29 (t, 2H), 6.51 (d, 1H), 5.54 (dd, 1H), 4.21 (dd, 1H), 3.80-3.61 (m, 1H), 3.55 (s, 3H), 3.51-3.41 (m, 4H), 2.09 (dd, 1H), 1.92 (dd, 1H), 1.57-1.42 (m, 1H), 1.36-1.25 (m, 1H), 1.22 (dd, 6H).

The invention claimed is:

1. A method for the preparation of a compound of general formula (2)

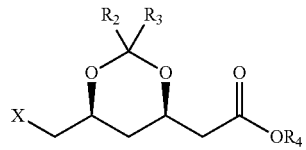

comprising contacting a compound of general formula (3)

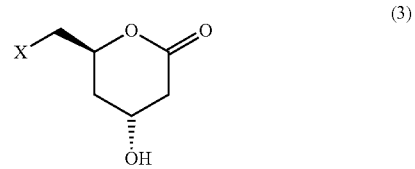

with an alcohol of general formula R₄—OH and an acetal or an alkoxy-alkene or a ketone in the presence of an acid wherein X is halogen and wherein R₂ and R₃ each independently stand for an alkyl with 1 to 12 carbon atoms, an alkenyl with 1 to 12 carbon atoms, a cycloalkyl with 3 to 7 carbon atoms, a cycloalkenyl with 3 to 7 carbon atoms, an aryl with 6 to 10 carbon atoms or an aralkyl with 7 to 12 carbon atoms, wherein each of R₂ and R₃ may be substituted and wherein R₂ and R₃ may form a ring together with the carbon atom to which they are bound, characterized in that R₄ is an alkyl or alkenyl group with 2 to 6 carbon atoms.

2. The method according to claim 1, wherein R₄ is allyl, iso-butenyl, n-butyl, sec-butyl, tert-butyl, ethyl, 2-methyl-3-pentyl, 4-methyl-1-pentyl, 4-methyl-2-pentyl, n-propyl, iso-propyl or vinyl.

3. The method according to claim 2, wherein said acetal is dimethoxypropane and said alkoxy-alkene is 2-ethoxypropene or 2-methoxypropene and said ketone is acetone or cyclohexanone or cyclopentanone or 3-pentanone.

4. The method according to claim 3, wherein X is bromine or chlorine and R₂ and R₃ are methyl.

* * * * *